(12) United States Patent
Park et al.

(10) Patent No.: US 7,998,508 B2
(45) Date of Patent: Aug. 16, 2011

(54) METHOD OF SCREENING PLACENTAL PROTEINS RESPONSIBLE FOR PATHOPHYSIOLOGY OF PREECLAMPSIA, AND MARKER FOR EARLY DIAGNOSIS AND PREDICTION OF PREECLAMPSIA

(75) Inventors: Won Sun Park, Busan (KR); Na Ri Kim, Busan (KR); Jin Han, Busan (KR)

(73) Assignee: Inje University Industry-Academic Cooperation Foundation, Gimhae (KR)

( * ) Notice: Subject to any disclaimer, the term of this patent is extended or adjusted under 35 U.S.C. 154(b) by 272 days.

(21) Appl. No.: 12/218,767

(22) Filed: Jul. 16, 2008

(65) Prior Publication Data
US 2009/0023168 A1    Jan. 22, 2009

(30) Foreign Application Priority Data
Jul. 16, 2007    (KR) .................. 10-2007-0071058

(51) Int. Cl.
*A61K 35/12*    (2006.01)
(52) U.S. Cl. ........................................ 424/520
(58) Field of Classification Search ............ None
See application file for complete search history.

(56) References Cited

OTHER PUBLICATIONS

Mine et al. "Proteome analysis of human placetae: pre-eclampsia versus normal pregnancy", Placenta, 2007, 28:676-687.*
Shankar et al. "An emerging role for comprehensive proteome analysis in human pregnancy research", Reproduction, 2005, 129:685-696.*

* cited by examiner

*Primary Examiner* — Jon P Weber
*Assistant Examiner* — Bin Shen
(74) *Attorney, Agent, or Firm* — Mannava & Kang, PC; Hyunho Park

(57) ABSTRACT

The present invention relates to a method of screening placental proteins responsible for pathophysiology of preeclampsia, and a marker for early diagnosis and prediction of preeclampsia. In accordance with one aspect of the present invention, there is provided a method of screening placental proteins responsible for pathophysiology of preeclampsia by 2D E-proteomics analysis, comprising: isolating placental proteins from a placental tissue; separating the isolated proteins two-dimensionally through 2D electrophoresis; and comparing and analyzing the separated proteins based on scanned gel images and differences in the images between normal placental proteins and preeclamptic placental proteins, wherein the comparison and analysis of the placental proteins based on the scanned gel images and differences in the images are accomplished by selecting proteins with differences of 140% or more between two placentas.

2 Claims, 4 Drawing Sheets
(4 of 4 Drawing Sheet(s) Filed in Color)

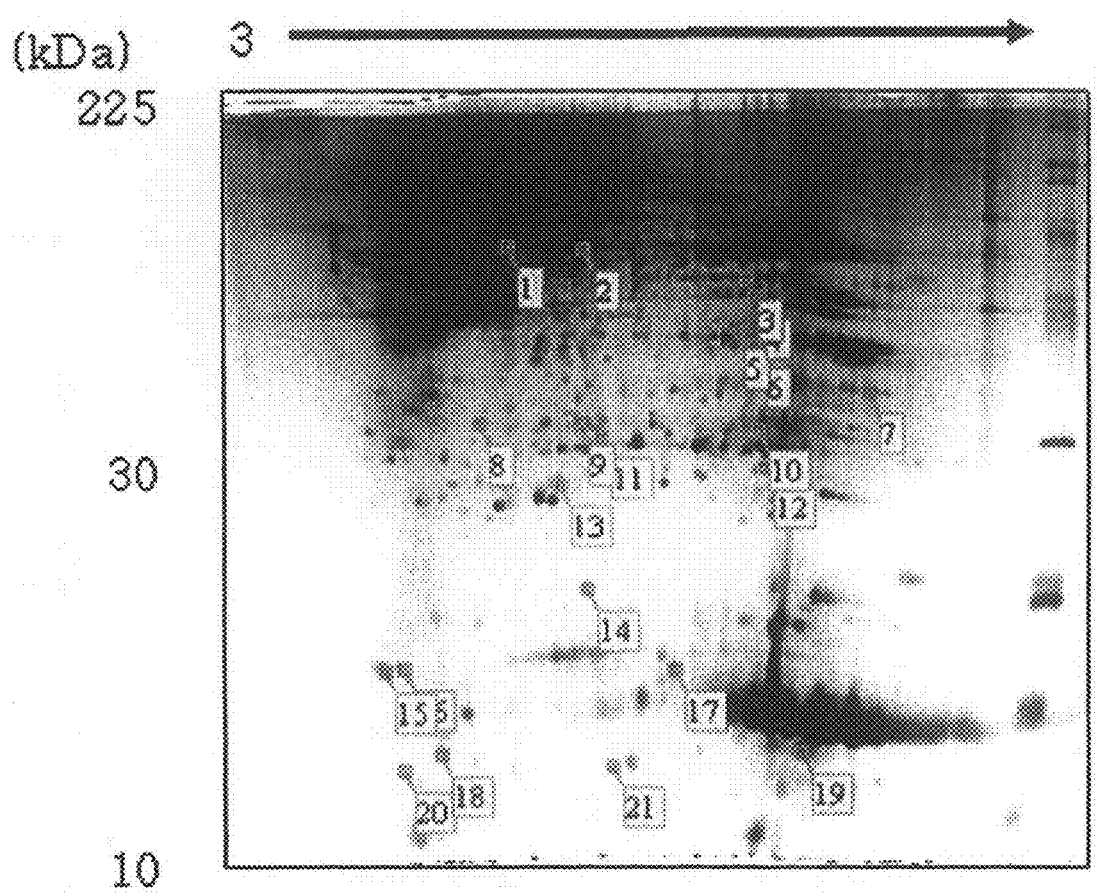

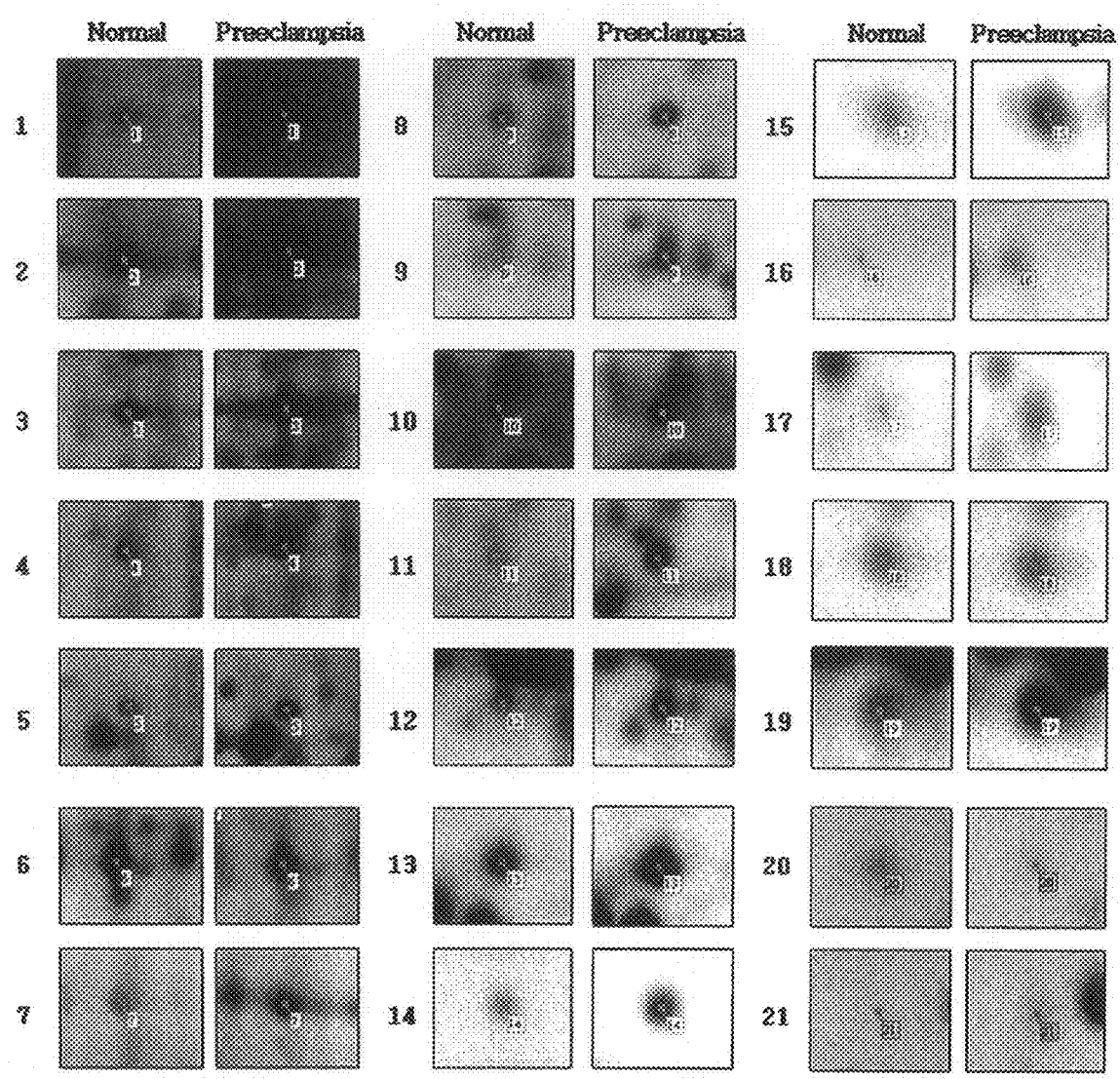

SEQUENCE LISTING

<160> NUMBER OF SEQ ID NOS: 16

<210> SEQ ID NO 1
<211> LENGTH: 573
<212> TYPE: PRT
<213> ORGANISM: Mus musculus

<400> SEQUENCE: 1

```
Met Leu Arg Leu Pro Thr Val Phe Arg Gln Met Arg Pro Val Ser Arg
  1               5                  10                  15

Val Leu Ala Pro His Leu Thr Arg Ala Tyr Ala Lys Asp Val Lys Phe
             20                  25                  30

Gly Ala Asp Ala Arg Ala Leu Met Leu Gln Gly Val Asp Leu Leu Ala
         35                  40                  45

Asp Ala Val Ala Val Thr Met Gly Pro Lys Gly Arg Thr Val Ile Ile
     50                  55                  60

Glu Gln Ser Trp Gly Ser Pro Lys Val Thr Lys Asp Gly Val Thr Val
 65                  70                  75                  80

Ala Lys Ser Ile Asp Leu Lys Asp Lys Tyr Lys Asn Ile Gly Ala Lys
                 85                  90                  95

Leu Val Gln Asp Val Ala Asn Asn Thr Asn Glu Ala Gly Asp Gly
            100                 105                 110

Thr Thr Thr Ala Thr Val Leu Ala Arg Ser Ile Ala Lys Glu Gly Phe
            115                 120                 125

Glu Lys Ile Ser Lys Gly Ala Asn Pro Val Glu Ile Arg Arg Gly Val
130                 135                 140

Met Leu Ala Val Asp Ala Val Ile Ala Glu Leu Lys Lys Gln Ser Lys
145                 150                 155                 160

Pro Val Thr Thr Pro Glu Glu Ile Ala Gln Val Ala Thr Ile Ser Ala
                165                 170                 175

Asn Gly Asp Lys Glu Ile Gly Asn Ile Ile Ser Asp Ala Met Lys Lys
            180                 185                 190

Val Gly Arg Lys Gly Val Ile Thr Val Lys Asp Gly Lys Thr Leu Asn
            195                 200                 205

Asp Glu Leu Glu Ile Ile Glu Gly Met Lys Phe Asp Arg Gly Tyr Ile
        210                 215                 220

Ser Pro Tyr Phe Ile Asn Thr Ser Lys Gly Gln Lys Cys Glu Phe Gln
225                 230                 235                 240

Asp Ala Tyr Val Leu Leu Ser Glu Lys Lys Ile Ser Ser Ile Gln Ser
                245                 250                 255

Ile Val Pro Ala Leu Glu Ile Ala Asn Ala His Arg Lys Pro Leu Val
            260                 265                 270

Ile Ile Ala Glu Asp Val Asp Gly Glu Ala Leu Ser Thr Leu Val Leu
        275                 280                 285

Asn Arg Leu Lys Val Gly Leu Gln Val Val Ala Val Lys Ala Pro Gly
    290                 295                 300

Phe Gly Asp Asn Arg Lys Asn Gln Leu Lys Asp Met Ala Ile Ala Thr
305                 310                 315                 320

Gly Gly Ala Val Phe Gly Glu Glu Gly Leu Thr Leu Asn Leu Glu Asp
                325                 330                 335

Val Gln Pro His Asp Leu Gly Lys Val Gly Glu Val Ile Val Thr Lys
            340                 345                 350

Asp Asp Ala Met Leu Leu Lys Gly Lys Gly Asp Lys Ala Gln Ile Glu
        355                 360                 365

Lys Arg Ile Gln Glu Ile Ile Glu Gln Leu Asp Val Thr Thr Ser Glu
    370                 375                 380

Tyr Glu Lys Glu Lys Leu Asn Glu Arg Leu Ala Lys Leu Ser Asp Gly
385                 390                 395                 400

Val Ala Val Leu Lys Val Gly Gly Thr Ser Asp Val Glu Val Asn Glu
                405                 410                 415
```

```
Lys Lys Asp Arg Val Thr Asp Ala Leu Asn Ala Thr Arg Ala Ala Val
            420                 425                 430

Glu Glu Gly Ile Val Leu Gly Gly Cys Ala Leu Leu Arg Cys Ile
            435                 440                 445

Pro Ala Leu Asp Ser Leu Thr Pro Ala Asn Glu Asp Gln Lys Ile Gly
450                 455                 460

Ile Glu Ile Ile Lys Arg Thr Leu Lys Ile Pro Ala Met Thr Ile Ala
465                 470                 475                 480

Lys Asn Ala Gly Val Glu Gly Ser Leu Ile Val Glu Lys Ile Met Gln
                    485                 490                 495

Ser Ser Ser Glu Val Gly Tyr Asp Ala Met Ala Gly Asp Phe Val Asn
            500                 505                 510

Met Val Glu Lys Gly Ile Ile Asp Pro Thr Lys Val Val Arg Thr Ala
            515                 520                 525

Leu Leu Asp Ala Ala Gly Val Ala Ser Leu Leu Thr Thr Ala Glu Val
            530                 535                 540

Val Val Thr Glu Ile Pro Lys Glu Glu Lys Asp Pro Gly Met Gly Ala
545                 550                 555                 560

Met Gly Gly Met Gly Gly Gly Met Gly Gly Gly Met Phe
                    565                 570

<210> SEQ ID NO 2
<211> LENGTH: 505
<212> TYPE: PRT
<213> ORGANISM: Homo sapiens

<400> SEQUENCE: 2

Met Arg Leu Arg Arg Leu Ala Leu Phe Pro Gly Val Ala Leu Leu Leu
1               5                   10                  15

Ala Ala Gly Arg Leu Val Ala Ala Ser Asp Val Leu Glu Leu Thr Asp
            20                  25                  30

Asp Asn Phe Glu Ser Arg Ile Ser Asp Thr Gly Ser Ala Gly Leu Met
            35                  40                  45

Leu Val Glu Phe Phe Ala Pro Trp Cys Gly His Cys Lys Arg Leu Ala
50                  55                  60

Pro Glu Tyr Glu Ala Ala Ala Thr Arg Leu Lys Gly Ile Val Pro Leu
65                  70                  75                  80

Ala Lys Val Asp Cys Thr Ala Asn Thr Asn Thr Cys Asn Lys Tyr Gly
                85                  90                  95

Val Ser Gly Tyr Pro Thr Leu Lys Ile Phe Arg Asp Gly Glu Glu Ala
            100                 105                 110

Gly Ala Tyr Asp Gly Pro Arg Thr Ala Asp Gly Ile Val Ser His Leu
            115                 120                 125

Lys Lys Gln Ala Gly Pro Ala Ser Val Pro Leu Arg Thr Glu Glu Glu
            130                 135                 140

Phe Lys Lys Phe Ile Ser Asp Lys Asp Ala Ser Ile Val Gly Phe Phe
145                 150                 155                 160

Asp Asp Ser Phe Ser Glu Ala His Ser Glu Phe Leu Lys Ala Ala Ser
                165                 170                 175

Asn Leu Arg Asp Asn Tyr Arg Phe Ala His Thr Asn Val Glu Ser Leu
            180                 185                 190

Val Asn Glu Tyr Asp Asp Asn Gly Glu Gly Ile Ile Leu Phe Arg Pro
            195                 200                 205

Ser His Leu Thr Asn Lys Phe Glu Asp Lys Thr Val Ala Tyr Thr Glu
210                 215                 220
```

```
Gln Lys Met Thr Ser Gly Lys Ile Lys Phe Ile Gln Glu Asn Ile
225                 230                 235                 240

Phe Gly Ile Cys Pro His Met Thr Glu Asp Asn Lys Asp Leu Ile Gln
            245                 250                 255

Gly Lys Asp Leu Leu Ile Ala Tyr Tyr Asp Val Asp Tyr Glu Lys Asn
                260                 265                 270

Ala Lys Gly Ser Asn Tyr Trp Arg Asn Arg Val Met Met Val Ala Lys
        275                 280                 285

Lys Phe Leu Asp Ala Gly His Lys Leu Asn Phe Ala Val Ala Ser Arg
    290                 295                 300

Lys Thr Phe Ser His Glu Leu Ser Asp Phe Gly Leu Glu Ser Thr Ala
305                 310                 315                 320

Gly Glu Ile Pro Val Val Ala Ile Arg Thr Ala Lys Gly Glu Lys Phe
                325                 330                 335

Val Met Gln Glu Glu Phe Ser Arg Asp Gly Lys Ala Leu Glu Arg Phe
                340                 345                 350

Leu Gln Asp Tyr Phe Asp Gly Asn Leu Lys Arg Tyr Leu Lys Ser Glu
            355                 360                 365

Pro Ile Pro Glu Ser Asn Asp Gly Pro Val Lys Val Val Ala Glu
370                 375                 380

Asn Phe Asp Glu Ile Val Asn Asn Glu Asn Lys Asp Val Leu Ile Glu
385                 390                 395                 400

Phe Tyr Ala Pro Trp Cys Gly His Cys Lys Asn Leu Glu Pro Lys Tyr
            405                 410                 415

Lys Glu Leu Gly Glu Lys Leu Ser Lys Asp Pro Asn Ile Val Ile Ala
            420                 425                 430

Lys Met Asp Ala Thr Ala Asn Asp Val Pro Ser Pro Tyr Glu Val Arg
            435                 440                 445

Gly Phe Pro Thr Ile Tyr Phe Ser Pro Ala Asn Lys Lys Leu Asn Pro
            450                 455                 460

Lys Lys Tyr Glu Gly Gly Arg Glu Leu Ser Asp Phe Ile Ser Tyr Leu
465                 470                 475                 480

Gln Arg Glu Ala Thr Asn Pro Pro Val Ile Gln Glu Glu Lys Pro Lys
                485                 490                 495

Lys Lys Lys Lys Ala Gln Glu Asp Leu
                500                 505

<210> SEQ ID NO 3
<211> LENGTH: 434
<212> TYPE: PRT
<213> ORGANISM: Homo sapiens

<400> SEQUENCE: 3

Met Ser Ile Leu Lys Ile His Ala Arg Glu Ile Phe Asp Ser Arg Gly
1               5                   10                  15

Asn Pro Thr Val Glu Val Asp Leu Phe Thr Ser Lys Gly Leu Phe Arg
                20                  25                  30

Ala Ala Val Pro Ser Gly Ala Ser Thr Gly Ile Tyr Glu Ala Leu Glu
            35                  40                  45

Leu Arg Asp Asn Asp Lys Thr Arg Tyr Met Gly Lys Gly Val Ser Lys
    50                  55                  60

Ala Val Glu His Ile Asn Lys Thr Ile Ala Pro Ala Leu Val Ser Lys
65                  70                  75                  80

Lys Leu Asn Val Thr Glu Gln Glu Lys Ile Asp Lys Leu Met Ile Glu
                85                  90                  95
```

-continued

```
Met Asp Gly Thr Glu Asn Lys Ser Lys Phe Gly Ala Asn Ala Ile Leu
            100                 105                 110
Gly Val Ser Leu Ala Val Cys Lys Ala Gly Ala Val Glu Lys Gly Val
        115                 120                 125
Pro Leu Tyr Arg His Ile Ala Asp Leu Ala Gly Asn Ser Glu Val Ile
    130                 135                 140
Leu Pro Val Pro Ala Phe Asn Val Ile Asn Gly Gly Ser His Ala Gly
145                 150                 155                 160
Asn Lys Leu Ala Met Gln Glu Phe Met Ile Leu Pro Val Gly Ala Ala
                165                 170                 175
Asn Phe Arg Glu Ala Met Arg Ile Gly Ala Glu Val Tyr His Asn Leu
            180                 185                 190
Lys Asn Val Ile Lys Glu Lys Tyr Gly Lys Asp Ala Thr Asn Val Gly
        195                 200                 205
Asp Glu Gly Gly Phe Ala Pro Asn Ile Leu Glu Asn Lys Glu Gly Leu
    210                 215                 220
Glu Leu Leu Lys Thr Ala Ile Gly Lys Ala Gly Tyr Thr Asp Lys Val
225                 230                 235                 240
Val Ile Gly Met Asp Val Ala Ala Ser Glu Phe Phe Arg Ser Gly Lys
                245                 250                 255
Tyr Asp Leu Asp Phe Lys Ser Pro Asp Asp Pro Ser Arg Tyr Ile Ser
            260                 265                 270
Pro Asp Gln Leu Ala Asp Leu Tyr Lys Ser Phe Ile Lys Asp Tyr Pro
        275                 280                 285
Val Val Ser Ile Glu Asp Pro Phe Asp Gln Asp Asp Trp Gly Ala Trp
    290                 295                 300
Gln Lys Phe Thr Ala Ser Ala Gly Ile Gln Val Val Gly Asp Asp Leu
305                 310                 315                 320
Thr Val Thr Asn Pro Lys Arg Ile Ala Lys Ala Val Asn Glu Lys Ser
                325                 330                 335
Cys Asn Cys Leu Leu Leu Lys Val Asn Gln Ile Gly Ser Val Thr Glu
            340                 345                 350
Ser Leu Gln Ala Cys Lys Leu Ala Gln Ala Asn Gly Trp Gly Val Met
        355                 360                 365
Val Ser His Arg Ser Gly Glu Thr Glu Asp Thr Phe Ile Ala Asp Leu
    370                 375                 380
Val Val Gly Leu Cys Thr Gly Gln Ile Lys Thr Gly Ala Pro Cys Arg
385                 390                 395                 400
Ser Glu Arg Leu Ala Lys Tyr Asn Gln Leu Leu Arg Ile Glu Glu Glu
                405                 410                 415
Leu Gly Ser Lys Ala Lys Phe Ala Gly Arg Asn Phe Arg Asn Pro Leu
            420                 425                 430
Ala Lys

<210> SEQ ID NO 4
<211> LENGTH: 414
<212> TYPE: PRT
<213> ORGANISM: Homo sapiens

<400> SEQUENCE: 4

Met Ser Lys Lys Ile Ser Gly Gly Ser Val Val Glu Met Gln Gly Asp
1               5                   10                  15
Glu Met Thr Arg Ile Ile Trp Glu Leu Ile Lys Glu Lys Leu Ile Phe
                20                  25                  30
```

```
Pro Tyr Val Glu Leu Asp Leu His Ser Tyr Asp Leu Gly Ile Glu Asn
         35                  40                  45

Arg Asp Ala Thr Asn Asp Gln Val Thr Lys Asp Ala Glu Ala Ile
 50                  55                  60

Lys Lys His Asn Val Gly Val Lys Cys Ala Thr Ile Thr Pro Asp Glu
 65                  70                  75                  80

Lys Arg Val Glu Glu Phe Lys Leu Lys Gln Met Trp Lys Ser Pro Asn
                 85                  90                  95

Gly Thr Ile Arg Asn Ile Leu Gly Gly Thr Val Phe Arg Glu Ala Ile
                100                 105                 110

Ile Cys Lys Asn Ile Pro Arg Leu Val Ser Gly Trp Val Lys Pro Ile
            115                 120                 125

Ile Ile Gly Arg His Ala Tyr Gly Asp Gln Tyr Arg Ala Thr Asp Phe
130                 135                 140

Val Val Pro Gly Pro Gly Lys Val Glu Ile Thr Tyr Thr Pro Ser Asp
145                 150                 155                 160

Gly Thr Gln Lys Val Thr Tyr Leu Val His Asn Phe Glu Glu Gly Gly
                165                 170                 175

Gly Val Ala Met Gly Met Tyr Asn Gln Asp Lys Ser Ile Glu Asp Phe
            180                 185                 190

Ala His Ser Ser Phe Gln Met Ala Leu Ser Lys Gly Trp Pro Leu Tyr
        195                 200                 205

Leu Ser Thr Lys Asn Thr Ile Leu Lys Lys Tyr Asp Gly Arg Phe Lys
210                 215                 220

Asp Ile Phe Gln Glu Ile Tyr Asp Lys Gln Tyr Lys Ser Gln Phe Glu
225                 230                 235                 240

Ala Gln Lys Ile Trp Tyr Glu His Arg Leu Ile Asp Asp Met Val Ala
                245                 250                 255

Gln Ala Met Lys Ser Glu Gly Gly Phe Ile Trp Ala Cys Lys Asn Tyr
            260                 265                 270

Asp Gly Asp Val Gln Ser Asp Ser Val Ala Gln Gly Tyr Gly Ser Leu
        275                 280                 285

Gly Met Met Thr Ser Val Leu Val Cys Pro Asp Gly Lys Thr Val Glu
290                 295                 300

Ala Glu Ala Ala His Gly Thr Val Thr Arg His Tyr Arg Met Tyr Gln
305                 310                 315                 320

Lys Gly Gln Glu Thr Ser Thr Asn Pro Ile Ala Ser Ile Phe Ala Trp
                325                 330                 335

Thr Arg Gly Leu Ala His Arg Ala Lys Leu Asp Asn Asn Lys Glu Leu
            340                 345                 350

Ala Phe Phe Ala Asn Ala Leu Glu Glu Val Ser Ile Glu Thr Ile Glu
        355                 360                 365

Ala Gly Phe Met Thr Lys Asp Leu Ala Ala Cys Ile Lys Gly Leu Pro
370                 375                 380

Asn Val Gln Arg Ser Asp Tyr Leu Asn Thr Phe Glu Phe Met Asp Lys
385                 390                 395                 400

Leu Gly Glu Asn Leu Lys Ile Lys Leu Ala Gln Ala Lys Leu
                405                 410

<210> SEQ ID NO 5
<211> LENGTH: 324
<212> TYPE: PRT
<213> ORGANISM: Homo sapiens
```

<400> SEQUENCE: 5

```
Ala Ala Ser Cys Val Leu Leu His Thr Gly Gln Lys Met Pro Leu Ile
1               5                   10                  15

Gly Leu Gly Thr Trp Lys Ser Glu Pro Gly Gln Val Lys Ala Ala Val
                20                  25                  30

Lys Tyr Ala Leu Ser Val Gly Tyr Arg His Ile Asp Cys Ala Ala Ile
            35                  40                  45

Tyr Gly Asn Glu Pro Glu Ile Gly Glu Ala Leu Lys Glu Asp Val Gly
    50                  55                  60

Pro Gly Lys Ala Val Pro Arg Glu Glu Leu Phe Val Thr Ser Lys Leu
65                  70                  75                  80

Trp Asn Thr Lys His His Pro Glu Asp Val Glu Pro Ala Leu Arg Lys
                85                  90                  95

Thr Leu Ala Asp Leu Gln Leu Glu Tyr Leu Asp Leu Tyr Leu Met His
            100                 105                 110

Trp Pro Tyr Ala Phe Glu Arg Gly Asp Asn Pro Phe Pro Lys Asn Ala
        115                 120                 125

Asp Gly Thr Ile Cys Tyr Asp Ser Thr His Tyr Lys Glu Thr Trp Lys
    130                 135                 140

Ala Leu Glu Ala Leu Val Ala Lys Gly Leu Val Gln Ala Leu Gly Leu
145                 150                 155                 160

Ser Asn Phe Asn Ser Arg Gln Ile Asp Asp Ile Leu Ser Val Ala Ser
                165                 170                 175

Val Arg Pro Ala Val Leu Gln Val Glu Cys His Pro Tyr Leu Ala Gln
            180                 185                 190

Asn Glu Leu Ile Ala His Cys Gln Ala Arg Gly Leu Glu Val Thr Ala
        195                 200                 205

Tyr Ser Pro Leu Gly Ser Ser Asp Arg Ala Trp Arg Asp Pro Asp Glu
    210                 215                 220

Pro Val Leu Leu Glu Glu Pro Val Val Leu Ala Leu Ala Glu Lys Tyr
225                 230                 235                 240

Gly Arg Ser Pro Ala Gln Ile Leu Leu Arg Trp Gln Val Gln Arg Lys
                245                 250                 255

Val Ile Cys Ile Pro Lys Ser Ile Thr Pro Ser Arg Ile Leu Gln Asn
            260                 265                 270

Ile Lys Val Phe Asp Phe Thr Phe Ser Pro Glu Glu Met Lys Gln Leu
        275                 280                 285

Asn Ala Leu Asn Lys Asn Trp Arg Tyr Ile Val Pro Met Leu Thr Val
    290                 295                 300

Asp Gly Lys Arg Val Pro Arg Asp Ala Gly His Pro Leu Tyr Pro Phe
305                 310                 315                 320

Asn Asp Pro Tyr
```

<210> SEQ ID NO 6
<211> LENGTH: 315
<212> TYPE: PRT
<213> ORGANISM: Homo sapiens

<400> SEQUENCE: 6

```
Ala Ser Arg Leu Leu Leu Asn Asn Gly Ala Lys Met Pro Ile Leu Gly
1               5                   10                  15

Leu Gly Thr Trp Lys Ser Pro Pro Gly Gln Val Thr Glu Ala Val Lys
                20                  25                  30

Val Ala Ile Asp Val Gly Tyr Arg His Ile Asp Cys Ala His Val Tyr
            35                  40                  45
```

```
Gln Asn Glu Asn Glu Val Gly Val Ala Ile Gln Glu Lys Leu Arg Glu
         50                  55                  60

Gln Val Val Lys Arg Glu Leu Phe Ile Val Ser Lys Leu Trp Cys
 65                  70                  75                  80

Thr Tyr His Glu Lys Gly Leu Val Lys Gly Ala Cys Gln Lys Thr Leu
                 85                  90                  95

Ser Asp Leu Lys Leu Asp Tyr Leu Asp Leu Tyr Leu Ile His Trp Pro
                100                 105                 110

Thr Gly Phe Lys Pro Gly Lys Glu Phe Phe Pro Leu Asp Glu Ser Gly
                115                 120                 125

Asn Val Val Pro Ser Asp Thr Asn Ile Leu Asp Thr Trp Ala Ala Met
                130                 135                 140

Glu Glu Leu Val Asp Glu Gly Leu Val Lys Ala Ile Gly Ile Ser Asn
145                 150                 155                 160

Phe Asn His Leu Gln Val Glu Met Ile Leu Asn Lys Pro Gly Leu Lys
                165                 170                 175

Tyr Lys Pro Ala Val Asn Gln Ile Glu Cys His Pro Tyr Leu Thr Gln
                180                 185                 190

Glu Lys Leu Ile Gln Tyr Cys Gln Ser Lys Gly Ile Val Val Thr Ala
                195                 200                 205

Tyr Ser Pro Leu Gly Ser Pro Asp Arg Pro Trp Ala Lys Pro Glu Asp
                210                 215                 220

Pro Ser Leu Leu Glu Asp Pro Arg Ile Lys Ala Ile Ala Ala Lys His
225                 230                 235                 240

Asn Lys Thr Thr Ala Gln Val Leu Ile Arg Phe Pro Met Gln Arg Asn
                245                 250                 255

Leu Val Val Ile Pro Lys Ser Val Thr Pro Glu Arg Ile Ala Glu Asn
                260                 265                 270

Phe Lys Val Phe Asp Phe Glu Leu Ser Ser Gln Asp Met Thr Thr Leu
                275                 280                 285

Leu Ser Tyr Asn Arg Asn Trp Arg Val Ser Ala Leu Leu Ser Cys Thr
                290                 295                 300

Ser His Lys Asp Tyr Pro Phe His Glu Glu Phe
305                 310                 315

<210> SEQ ID NO 7
<211> LENGTH: 315
<212> TYPE: PRT
<213> ORGANISM: Gallus gallus

<400> SEQUENCE: 7

Ala Ser Arg Leu Leu Asn Asn Gly Ala Lys Met Pro Ile Leu Gly
 1               5                  10                  15

Leu Gly Thr Trp Lys Ser Pro Gly Gln Val Thr Glu Ala Val Lys
                 20                  25                  30

Val Ala Ile Asp Val Gly Tyr Arg His Ile Asp Cys Ala His Val Tyr
                 35                  40                  45

Gln Asn Glu Asn Glu Val Gly Val Ala Ile Gln Glu Lys Leu Arg Glu
         50                  55                  60

Gln Val Val Lys Arg Glu Leu Phe Ile Val Ser Lys Leu Trp Cys
 65                  70                  75                  80

Thr Tyr His Glu Lys Gly Leu Val Lys Gly Ala Cys Gln Lys Thr Leu
                 85                  90                  95

Ser Asp Leu Lys Leu Asp Tyr Leu Asp Leu Tyr Leu Ile His Trp Pro
                100                 105                 110
```

-continued

```
Thr Gly Phe Lys Pro Gly Lys Glu Phe Phe Pro Leu Asp Glu Ser Gly
            115                 120                 125

Asn Val Val Pro Ser Asp Thr Asn Ile Leu Asp Thr Trp Ala Ala Met
        130                 135                 140

Glu Glu Leu Val Asp Glu Gly Leu Val Lys Ala Ile Gly Ile Ser Asn
145                 150                 155                 160

Phe Asn His Leu Gln Val Glu Met Ile Leu Asn Lys Pro Gly Leu Lys
                165                 170                 175

Tyr Lys Pro Ala Val Asn Gln Ile Glu Cys His Pro Tyr Leu Thr Gln
            180                 185                 190

Glu Lys Leu Ile Gln Tyr Cys Gln Ser Lys Gly Ile Val Val Thr Ala
        195                 200                 205

Tyr Ser Pro Leu Gly Ser Pro Asp Arg Pro Trp Ala Lys Pro Glu Asp
210                 215                 220

Pro Ser Leu Leu Glu Asp Pro Arg Ile Lys Ala Ile Ala Ala Lys His
225                 230                 235                 240

Asn Lys Thr Thr Ala Gln Val Leu Ile Arg Phe Pro Met Gln Arg Asn
                245                 250                 255

Leu Val Val Ile Pro Lys Ser Val Thr Pro Glu Arg Ile Ala Glu Asn
            260                 265                 270

Phe Lys Val Phe Asp Phe Glu Leu Ser Ser Gln Asp Met Thr Thr Leu
        275                 280                 285

Leu Ser Tyr Asn Arg Asn Trp Arg Val Ser Ala Leu Leu Ser Cys Thr
290                 295                 300

Ser His Lys Asp Tyr Pro Phe His Glu Glu Phe
305                 310                 315

<210> SEQ ID NO 8
<211> LENGTH: 241
<212> TYPE: PRT
<213> ORGANISM: Homo sapiens

<400> SEQUENCE: 8

Met Ala Glu Glu Gln Pro Gln Val Glu Leu Phe Val Lys Ala Gly Ser
1               5                   10                  15

Asp Gly Ala Lys Ile Gly Asn Cys Pro Phe Ser Gln Arg Leu Phe Met
            20                  25                  30

Val Leu Trp Leu Lys Gly Val Thr Phe Asn Val Thr Thr Val Asp Thr
        35                  40                  45

Lys Arg Arg Thr Glu Thr Val Gln Lys Leu Cys Pro Gly Gly Glu Leu
    50                  55                  60

Pro Phe Leu Leu Tyr Gly Thr Glu Val His Thr Asp Thr Asn Lys Ile
65                  70                  75                  80

Glu Glu Phe Leu Glu Ala Val Leu Cys Pro Pro Arg Tyr Pro Lys Leu
                85                  90                  95

Ala Ala Leu Asn Pro Glu Ser Asn Thr Ala Gly Leu Asp Ile Phe Ala
            100                 105                 110

Lys Phe Ser Ala Tyr Ile Lys Asn Ser Asn Pro Ala Leu Asn Asp Asn
        115                 120                 125

Leu Glu Lys Gly Leu Leu Lys Ala Leu Lys Val Leu Asp Asn Tyr Leu
    130                 135                 140

Thr Ser Pro Leu Pro Glu Glu Val Asp Glu Thr Ser Ala Glu Asp Glu
145                 150                 155                 160

Gly Val Ser Gln Arg Lys Phe Leu Asp Gly Asn Glu Leu Thr Leu Ala
                165                 170                 175
```

-continued

```
Asp Cys Asn Leu Leu Pro Lys Leu His Ile Val Gln Val Val Cys Lys
            180                 185                 190

Lys Tyr Arg Gly Phe Thr Ile Pro Glu Ala Phe Arg Gly Val His Arg
        195                 200                 205

Tyr Leu Ser Asn Ala Tyr Ala Arg Glu Glu Phe Ala Ser Thr Cys Pro
    210                 215                 220

Asp Asp Glu Glu Ile Glu Leu Ala Tyr Glu Gln Val Ala Lys Ala Leu
225                 230                 235                 240

Lys

<210> SEQ ID NO 9
<211> LENGTH: 241
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Any amino acid

<400> SEQUENCE: 9

Xaa Gly Val Lys Val Glu Arg Gln Val Phe Gly Glu Ala Thr Lys Gln
1               5                  10                  15

Pro Gly Ile Thr Phe Ile Ala Ala Lys Phe Asp Gly Ile Leu Gly Met
            20                  25                  30

Ala Tyr Pro Arg Ile Ser Val Asn Asn Val Leu Pro Val Phe Asp Asn
        35                  40                  45

Leu Met Gln Gln Lys Leu Val Asp Gln Asn Ile Phe Ser Phe Tyr Leu
    50                  55                  60

Ser Arg Asp Pro Asp Ala Gln Pro Gly Gly Glu Leu Met Leu Gly Gly
65                  70                  75                  80

Thr Asp Ser Lys Tyr Tyr Lys Gly Ser Leu Ser Tyr Leu Asn Val Thr
                85                  90                  95

Arg Lys Ala Tyr Trp Gln Val His Leu Asp Gln Val Glu Val Ala Ser
            100                 105                 110

Gly Leu Thr Leu Cys Lys Glu Gly Cys Glu Ala Ile Val Asp Thr Gly
        115                 120                 125

Thr Ser Leu Met Val Gly Pro Val Asp Glu Val Arg Glu Leu Gln Lys
    130                 135                 140

Ala Ile Gly Ala Val Pro Leu Ile Gln Gly Glu Tyr Met Ile Pro Cys
145                 150                 155                 160

Glu Lys Val Ser Thr Leu Pro Ala Ile Thr Leu Lys Leu Gly Gly Lys
                165                 170                 175

Gly Tyr Lys Leu Ser Pro Glu Asp Tyr Thr Leu Lys Val Ser Gln Ala
            180                 185                 190

Gly Lys Thr Leu Cys Leu Ser Gly Phe Met Gly Met Asp Ile Pro Pro
        195                 200                 205

Pro Ser Gly Pro Leu Trp Ile Leu Gly Asp Val Phe Ile Gly Arg Tyr
    210                 215                 220

Tyr Thr Val Phe Asp Arg Asp Asn Asn Arg Val Gly Phe Ala Glu Ala
225                 230                 235                 240

Ala

<210> SEQ ID NO 10
<211> LENGTH: 254
<212> TYPE: PRT
<213> ORGANISM: Homo sapiens
```

-continued

<400> SEQUENCE: 10

```
Met Ala Ala Tyr Lys Leu Val Leu Ile Arg His Gly Glu Ser Ala Trp
1               5                   10                  15

Asn Leu Glu Asn Arg Phe Ser Gly Trp Tyr Asp Ala Asp Leu Ser Pro
            20                  25                  30

Ala Gly His Glu Glu Ala Lys Arg Gly Gly Gln Ala Leu Arg Asp Ala
        35                  40                  45

Gly Tyr Glu Phe Asp Ile Cys Phe Thr Ser Val Gln Lys Arg Ala Ile
    50                  55                  60

Arg Thr Leu Trp Thr Val Leu Asp Ala Ile Asp Gln Met Trp Leu Pro
65                  70                  75                  80

Val Val Arg Thr Trp Arg Leu Asn Glu Arg His Tyr Gly Gly Leu Thr
                85                  90                  95

Gly Leu Asn Lys Ala Glu Thr Ala Ala Lys His Gly Glu Ala Gln Val
            100                 105                 110

Lys Ile Trp Arg Arg Ser Tyr Asp Val Pro Pro Pro Met Glu Pro
        115                 120                 125

Asp His Pro Phe Tyr Ser Asn Ile Ser Lys Asp Arg Arg Tyr Ala Asp
    130                 135                 140

Leu Thr Glu Asp Gln Leu Pro Ser Cys Glu Ser Leu Lys Asp Thr Ile
145                 150                 155                 160

Ala Arg Ala Leu Pro Phe Trp Asn Glu Glu Ile Val Pro Gln Ile Lys
                165                 170                 175

Glu Gly Lys Arg Val Leu Ile Ala Ala His Gly Asn Ser Leu Arg Gly
            180                 185                 190

Ile Val Lys His Leu Glu Gly Leu Ser Glu Glu Ala Ile Met Glu Leu
        195                 200                 205

Asn Leu Pro Thr Gly Ile Pro Ile Val Tyr Glu Leu Asp Lys Asn Leu
    210                 215                 220

Lys Pro Ile Lys Pro Met Gln Phe Leu Gly Asp Glu Glu Thr Val Arg
225                 230                 235                 240

Lys Ala Met Glu Ala Val Ala Ala Gln Gly Lys Ala Lys Lys
                245                 250
```

<210> SEQ ID NO 11
<211> LENGTH: 261
<212> TYPE: PRT
<213> ORGANISM: Homo sapiens

<400> SEQUENCE: 11

```
Met Ala Ala Ala Val Pro Arg Ala Ala Phe Leu Ser Pro Leu Leu Pro
1               5                   10                  15

Leu Leu Leu Gly Phe Leu Leu Ser Ala Pro His Gly Gly Ser Gly
            20                  25                  30

Leu His Thr Lys Gly Ala Leu Pro Leu Asp Thr Val Thr Phe Tyr Lys
        35                  40                  45

Val Ile Pro Lys Ser Lys Phe Val Leu Val Lys Phe Asp Thr Gln Tyr
    50                  55                  60

Pro Tyr Gly Glu Lys Gln Asp Glu Phe Lys Arg Leu Ala Glu Asn Ser
65                  70                  75                  80

Ala Ser Ser Asp Asp Leu Leu Val Ala Glu Val Gly Ile Ser Asp Tyr
                85                  90                  95

Gly Asp Lys Leu Asn Met Glu Leu Ser Glu Lys Tyr Lys Leu Asp Lys
            100                 105                 110
```

Glu Ser Tyr Pro Val Phe Tyr Leu Phe Arg Asp Gly Asp Phe Glu Asn
            115                 120                 125

Pro Val Pro Tyr Thr Gly Ala Val Lys Val Gly Ala Ile Gln Arg Trp
130                 135                 140

Leu Lys Gly Gln Gly Val Tyr Leu Gly Met Pro Gly Cys Leu Pro Val
145                 150                 155                 160

Tyr Asp Ala Leu Ala Gly Glu Phe Ile Arg Ala Ser Gly Val Glu Ala
                165                 170                 175

Arg Gln Ala Leu Leu Lys Gln Gly Gln Asp Asn Leu Ser Ser Val Lys
            180                 185                 190

Glu Thr Gln Lys Lys Trp Ala Glu Gln Tyr Leu Lys Ile Met Gly Lys
        195                 200                 205

Ile Leu Asp Gln Gly Glu Asp Phe Pro Ala Ser Glu Met Thr Arg Ile
    210                 215                 220

Ala Arg Leu Ile Glu Lys Asn Lys Met Ser Asp Gly Lys Lys Glu Glu
225                 230                 235                 240

Leu Gln Lys Ser Leu Asn Ile Leu Thr Ala Phe Gln Lys Lys Gly Ala
                245                 250                 255

Glu Lys Glu Glu Leu
            260

<210> SEQ ID NO 12
<211> LENGTH: 234
<212> TYPE: PRT
<213> ORGANISM: Mus musculus

<400> SEQUENCE: 12

Met Ala Glu Arg Gly Tyr Ser Phe Ser Leu Thr Thr Phe Ser Pro Ser
1               5                   10                  15

Gly Lys Leu Val Gln Ile Glu Tyr Ala Leu Ala Ala Val Ala Gly Gly
            20                  25                  30

Ala Pro Ser Val Gly Ile Lys Ala Ala Asn Gly Val Val Leu Ala Thr
        35                  40                  45

Glu Lys Lys Gln Lys Ser Ile Leu Tyr Asp Glu Arg Ser Val His Lys
    50                  55                  60

Val Glu Pro Ile Thr Lys His Ile Gly Leu Val Tyr Ser Gly Met Gly
65                  70                  75                  80

Pro Asp Tyr Arg Val Leu Val His Arg Ala Arg Lys Leu Ala Gln Gln
                85                  90                  95

Tyr Tyr Leu Val Tyr Gln Glu Pro Ile Pro Thr Ala Gln Leu Val Gln
            100                 105                 110

Arg Val Ala Ser Val Met Gln Glu Tyr Thr Gln Ser Gly Gly Val Arg
        115                 120                 125

Pro Phe Gly Val Ser Leu Leu Ile Cys Gly Trp Asn Glu Gly Arg Pro
    130                 135                 140

Tyr Leu Phe Gln Ser Asp Pro Ser Gly Ala Tyr Phe Ala Trp Lys Ala
145                 150                 155                 160

Thr Ala Met Gly Lys Asn Tyr Val Asn Gly Lys Thr Phe Leu Glu Lys
                165                 170                 175

Arg Tyr Asn Glu Asp Leu Glu Leu Glu Asp Ala Ile His Thr Ala Ile
            180                 185                 190

Leu Thr Leu Lys Glu Ser Phe Glu Gly Gln Met Thr Glu Asp Asn Ile
        195                 200                 205

```
Glu Val Gly Ile Cys Asn Glu Ala Gly Phe Arg Arg Leu Thr Pro Thr
    210                 215                 220
Glu Val Lys Asp Tyr Leu Ala Ala Ile Ala
225                 230
```

<210> SEQ ID NO 13
<211> LENGTH: 210
<212> TYPE: PRT
<213> ORGANISM: Homo sapiens

<400> SEQUENCE: 13

```
Met Pro Pro Tyr Thr Val Val Tyr Phe Pro Val Arg Gly Arg Cys Ala
1               5                   10                  15
Ala Leu Arg Met Leu Leu Ala Asp Gln Gly Gln Ser Trp Lys Glu Glu
            20                  25                  30
Val Val Thr Val Glu Thr Trp Gln Glu Gly Ser Leu Lys Ala Ser Cys
        35                  40                  45
Leu Tyr Gly Gln Leu Pro Lys Phe Gln Asp Gly Asp Leu Thr Leu Tyr
    50                  55                  60
Gln Ser Asn Thr Ile Leu Arg His Leu Gly Arg Thr Leu Gly Leu Tyr
65                  70                  75                  80
Gly Lys Asp Gln Gln Glu Ala Ala Leu Val Asp Met Val Asn Asp Gly
                85                  90                  95
Val Glu Asp Leu Arg Cys Lys Tyr Ile Ser Leu Ile Tyr Thr Asn Tyr
            100                 105                 110
Glu Ala Gly Lys Asp Asp Tyr Val Lys Ala Leu Pro Gly Gln Leu Lys
        115                 120                 125
Pro Phe Glu Thr Leu Leu Ser Gln Asn Gln Gly Gly Lys Thr Phe Ile
    130                 135                 140
Val Gly Asp Gln Ile Ser Phe Ala Asp Tyr Asn Leu Leu Asp Leu Leu
145                 150                 155                 160
Leu Ile His Glu Val Leu Ala Pro Gly Cys Leu Asp Ala Phe Pro Leu
                165                 170                 175
Leu Ser Ala Tyr Val Gly Arg Leu Ser Pro Arg Pro Lys Leu Lys Ala
            180                 185                 190
Phe Leu Ala Ser Pro Glu Tyr Val Asn Leu Pro Ile Asn Gly Asn Gly
        195                 200                 205
Lys Gln
    210
```

<210> SEQ ID NO 14
<211> LENGTH: 111
<212> TYPE: PRT
<213> ORGANISM: Mus musculus

<400> SEQUENCE: 14

```
Val Asp Gly Ser Leu Arg Leu Ser Cys Ala Ala Ser Gly Phe Thr Phe
1               5                   10                  15
Ser His Tyr Ala Val His Trp Val Arg Gln Ala Pro Gly Lys Gly Leu
            20                  25                  30
Glu Trp Leu Ala Phe Ile Ser Ala Asp Gly Ser Asp Thr Asp His Ala
        35                  40                  45
Pro Ser Val Lys Gly Arg Phe Thr Ile Ser Arg Asp Asn Ser Arg Asn
    50                  55                  60
Met Leu Phe Leu Gln Met Asn Asn Val Arg Val Asp Asp Thr Ala Val
65                  70                  75                  80
```

```
Tyr Tyr Cys Ala Arg Glu Tyr Gly Arg Asp Tyr Asp Tyr Gly Thr
                85                  90                  95

Tyr Tyr Tyr Asp Ser Trp Gly Arg Gly Thr Leu Val Thr Val Asp
            100                 105                 110
```

<210> SEQ ID NO 15
<211> LENGTH: 151
<212> TYPE: PRT
<213> ORGANISM: Homo sapiens

<400> SEQUENCE: 15

```
Met Cys Asp Phe Thr Glu Asp Gln Thr Ala Glu Phe Lys Glu Ala Phe
1               5                   10                  15

Gln Leu Phe Asp Arg Thr Gly Asp Gly Lys Ile Leu Tyr Ser Gln Cys
                20                  25                  30

Gly Asp Val Met Arg Ala Leu Gly Gln Asn Pro Thr Asn Ala Glu Val
            35                  40                  45

Leu Lys Val Leu Gly Asn Pro Lys Ser Asp Glu Met Asn Val Lys Val
50                  55                  60

Leu Asp Phe Glu His Phe Leu Pro Met Leu Gln Thr Val Ala Lys Asn
65                  70                  75                  80

Lys Asp Gln Gly Thr Tyr Glu Asp Tyr Val Glu Gly Leu Arg Val Phe
                85                  90                  95

Asp Lys Glu Gly Asn Gly Thr Val Met Gly Ala Glu Ile Arg His Val
            100                 105                 110

Leu Val Thr Leu Gly Glu Lys Met Thr Glu Glu Glu Val Glu Met Leu
        115                 120                 125

Val Ala Gly His Glu Asp Ser Asn Gly Cys Ile Asn Tyr Glu Ala Phe
    130                 135                 140

Val Arg His Ile Leu Ser Gly
145                 150
```

<210> SEQ ID NO 16
<211> LENGTH: 135
<212> TYPE: PRT
<213> ORGANISM: Homo sapiens

<400> SEQUENCE: 16

```
Met Ala Thr Val Gln Gln Leu Glu Gly Arg Trp Arg Leu Val Asp Ser
1               5                   10                  15

Lys Gly Phe Asp Glu Tyr Met Lys Glu Leu Gly Val Gly Ile Ala Leu
                20                  25                  30

Arg Lys Met Gly Ala Met Ala Lys Pro Asp Cys Ile Ile Thr Cys Asp
            35                  40                  45

Gly Lys Asn Leu Thr Ile Lys Thr Glu Ser Thr Leu Lys Thr Thr Gln
50                  55                  60

Phe Ser Cys Thr Leu Gly Glu Lys Phe Glu Glu Thr Thr Ala Asp Gly
65                  70                  75                  80

Arg Lys Thr Gln Thr Val Cys Asn Phe Thr Asp Gly Ala Leu Val Gln
                85                  90                  95

His Gln Glu Trp Asp Gly Lys Glu Ser Thr Ile Thr Arg Lys Leu Lys
            100                 105                 110

Asp Gly Lys Leu Val Val Glu Cys Val Met Asn Asn Val Thr Cys Thr
        115                 120                 125

Arg Ile Tyr Glu Lys Val Glu
    130                 135
```

METHOD OF SCREENING PLACENTAL PROTEINS RESPONSIBLE FOR PATHOPHYSIOLOGY OF PREECLAMPSIA, AND MARKER FOR EARLY DIAGNOSIS AND PREDICTION OF PREECLAMPSIA

SEQUENCE LISTING

The instant application contains a Sequence Listing which has been submitted via EFS-Web and is hereby incorporated by reference in its entirety. Said ASCII copy, created on Jul. 27, 2010, is named 1029007.txt and is 41,676 bytes in size.

FIELD OF THE INVENTION

The present invention relates to a method of screening placental proteins responsible for pathophysiology of preeclampsia, and a marker for early diagnosis and prediction of preeclampsia.

BACKGROUND OF THE INVENTION

Preeclampsia in pregnancy can be a very serious health problem. It can cause fetal growth restriction, fetal death and morbidity, premature deliveries, and death of the mother. The exact cause of preeclampsia is not known, and treatments for efficiently curing or preventing preeclampsia are not also available yet. Preeclampsia is known to cause several problems at the same time, such as high blood pressure (hypertension), pathological edema and leakage of protein into the urine (proteinuria). Further, preeclampsia is one of the pregnancy complications that bring hypertension, proteinuria and traumatism to the mother. It is known that preeclampsia occurs to only about 3-5% of pregnant women, but it can seriously affect both the mother and her unborn (or newborn) baby, and thus, acts as a major cause of increasing perinatal mortality and morbidity rates.

Globally, at least 200,000 pregnant women die from preeclampsia every year. Its symptoms typically become evident after the $20^{th}$ week of pregnancy. Preeclampsia is usually diagnosed by detecting high blood pressure of a pregnant woman or by checking her urine for protein. Early diagnosis and timely treatment of preeclampsia can remarkably reduce risks to the mother and her unborn baby, but such a monitoring method by using those symptoms as criteria is not effective for an early diagnosis of preeclampsia. Further, no treatments are currently available to cure preeclampsia. Preeclampsia can be mild, but potentially life-threatening depending on the severity of the disease. Despite such clinical risks, however, it is difficult to find the cause or the pathogenesis of preeclampsia at an early stage, or to make an early diagnosis and prognosis.

Therefore, if it becomes possible to suggest the pathogenesis of preeclampsia and make an early diagnosis and prognosis based on the same, the mother having preeclampsia and her unborn baby can be protected, and the death rate would be reduced. Even if many researches have been conducted to monitor and predict the occurrence of preeclampsia, they are limited to using a specific protein or substance, which is not sufficient to explain the whole phenomenon about the occurrence of preeclampsia and the pathogenesis thereof.

While the inventors of the present invention have been trying to discover the pathogenesis of preeclampsia, they checked entire protein expressions in a placenta that plays a key role in the onset of preeclampsia and analyzed any change in the protein expressions in a preeclamptic placenta. Based on this, they devised a method of screening placental proteins responsible for pathophysiology of preeclampsia and a marker for early diagnosis and prediction of preeclampsia and also suggested a comprehensive theory of the pathogenesis of preeclampsia to complete the present invention.

SUMMARY OF THE INVENTION

It is, therefore, a primary object of the present invention to provide a method of screening placental proteins responsible for pathophysiology of preeclampsia.

It is another object of the present invention to provide a marker protein for early diagnosis and prediction of preeclampsia.

In accordance with one aspect of the present invention, there is provided a method of screening placental proteins responsible for pathophysiology of preeclampsia by 2D E-proteomics analysis, comprising: isolating placental proteins from a placental tissue; separating the isolated proteins two-dimensionally through 2D electrophoresis; and comparing and analyzing the separated proteins based on scanned gel images and differences in the images between normal placental proteins and preeclamptic placental proteins, wherein the comparison and analysis of the placental proteins based on the scanned gel images and differences in the images are accomplished by selecting proteins with differences of 140% or more between two placentas.

In accordance with another aspect of the present invention, there is provided a marker for early diagnosis and prediction of preeclampsia, comprising one or more proteins selected from the protein group consisting of chaperonin, ER-60 protease, isocitrate dehydrogenase 1, aldehyde reductase 1, fidaresta chain B bonded to human aldose reductase, voltage-dependent anion channel 1, nuclear chloride channel, cathepsin D chain H, phosphoglycerate mutase 1, endoplasmic reticulum protein, PSMA2 protein, glutathione S-transferase, Ig heavy chain v region, smooth muscle myosin alkali light chain, and fatty acid binding protein.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The above and other objects and features of the present invention will become apparent from the following description of the preferred examples given in conjunction with the accompanying drawings, in which:

FIG. 1 shows 2-D gel E-proteomics analysis pictures taken for the identification of changes in placental proteins of a pregnant woman with preeclampsia, in which FIG. 1A is a gel picture of placental proteins in normal pregnancy and FIG. 1B is a gel picture of placental proteins in pregnancy with preeclampsia;

FIG. 2 presents comparative pictures of 21 proteins which show big differences in expression between normal placenta and preeclamptic placenta (left-hand side: normal cell; right-hand side: gastric cancer cell) in result of the E-proteomics analysis depicted in FIG. 1.

DETAILED DESCRIPTION OF THE PREFERRED EMBODIMENTS

Figure 1A:
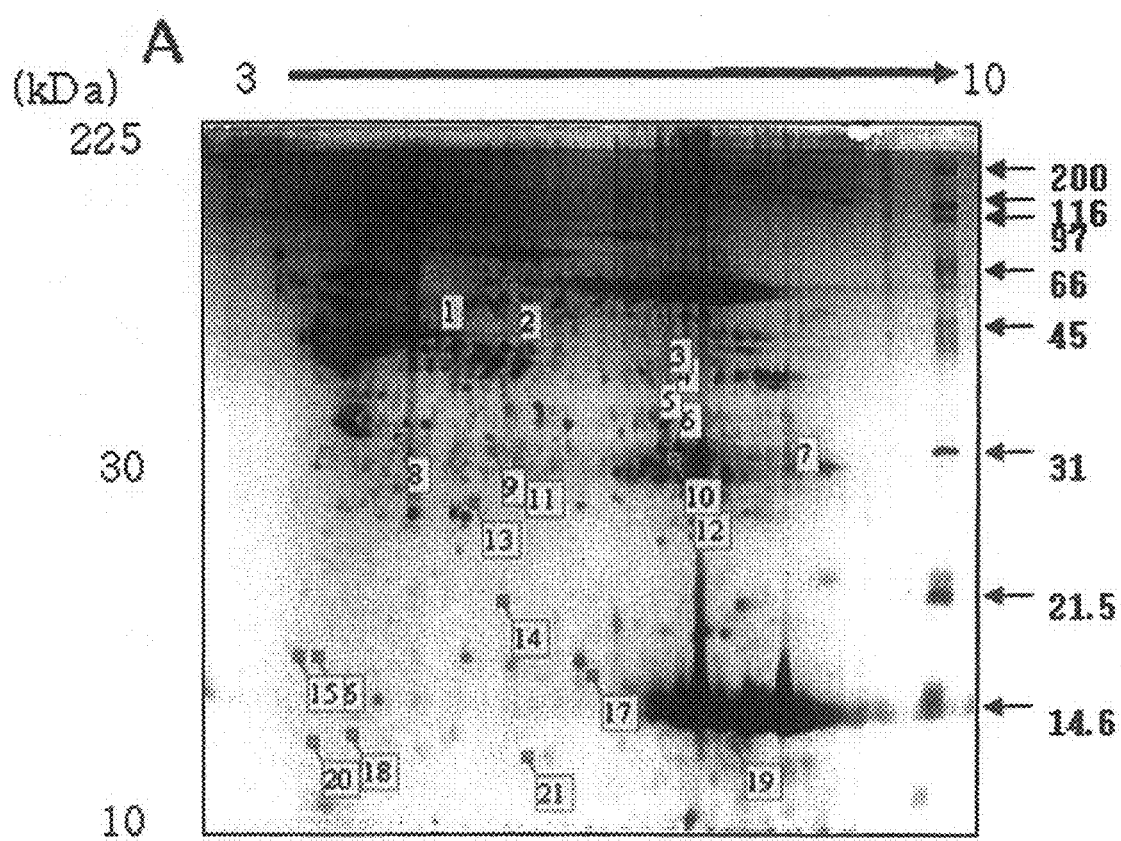

In the following detailed description, reference is made to the accompanying drawings that show, by way of illustration, specific embodiments in which the invention may be practiced. These embodiments are described in sufficient detail to enable those skilled in the art to practice the invention. It is to be understood that the various embodiments of the invention, although different, are not necessarily mutually exclusive. The following detailed description is, therefore, not to be taken in a limiting sense, and the scope of the present invention is defined only by the appended claims that should be appropriately interpreted along with the full range of equivalents to which the claims are entitled.

Then, experiments performed for better understanding the present invention will be described in detail as follows, which are set forth to illustrate, but are not to be construed to limit the present invention.

Hereinafter, the present invention will be described in more detail.

The present invention is directed to analyzing protein expression in preeclamptic placenta. More specifically, the present invention is directed to analyzing placental proteins that demonstrate more changes in expression in preeclamptic pregnancy than in normal pregnancy, thus identifying proteins responsible for pathophysiology of preeclampsia.

In order to identify proteins associated with pathophysiology of preeclampsia, the inventors conducted 2D E-proteomics analysis on the expression of placental proteins, and compared protein expression in a normal placenta and in a preeclamptic placenta to verify the differences in protein expression between them. The "2D E-proteomics analysis" perceives cell or tissue proteins in a packet and identifies an overall change, not individual changes, in proteins reflected in electrical and physical natures proved by electrophoresis. This research method is now actively being used worldwide and is largely composed of primary separation of proteins by isoelectric point and secondary gel-based protein separation by molecular mass. Images of proteins that are broadly distributed over the gel through the two-step protein separation technique were analyzed by an image analyzer for comparison of quantitative expression of proteins. Among them, proteins showing big differences were collected, and molecular weight in unit of peptide (a small cut piece of protein) of which were measured by a molecular weight measurement technique called MALDI-TOF MS. Each of the measured peptide masses was again calculated in terms of the mass of amino acids constituting a peptide. The final masses were compared with those in the already known peptide mass database to prove nature of original proteins.

The present invention suggests, based on the 2D E-proteomics analysis, 21 proteins demonstrating big differences in expression in a preeclamptic placenta. These proteins may be used for explaining abnormal metabolism in a preeclamptic placenta and its pathophysiology. Further, the proteins are expected to be effectively used for early diagnosis and prediction of preeclampsia in pregnant women.

For the 2D E-proteomics analysis, the inventors obtained normal placenta tissues and preeclamptic placenta tissues and separated placental proteins according to their isoelectric point (the primary separation step) and according to their molecular weight (the secondary separation step). The gel obtained after electrophoresis was stained by silver nitrate. Then, the stained gel was scanned with a flatbed scanner and analyzed through an image analysis program. Proteins showing differences of 140% or more in two groups of placental samples were selected and finally identified. Twenty one proteins were collected and peaks of protein mass spectrometry were searched by MASCOT PMF based on the NCBI database (see Table 1). Seventeen out of those twenty one proteins were analyzed, and most of them were identified as ones associated with placental metabolism (see Table 2). These proteins may be categorized into different types on the basis of their association with antioxidant activities, recombination related to stress, apoptosis, glycolysis, immunomodulation, or remodeling of reduced NADP, such that the pathophysiology of protein-underlying preeclampsia can be presented (see FIG. 3).

Hereinafter, the present invention will be explained in more detail through examples. However, it will be apparent to those skilled in the art that these examples are only for the purpose of explaining the present invention in detail, but not intended to limit the scope of the invention.

Example 1

Separation of Placental Proteins

Normal placenta and preeclamptic placenta were prepared for 2D E-proteomics analysis. Placental tissues were ground to fine powder in presence of liquid nitrogen, and a buffer (tissue: 0.2 g/10 ml) was added thereto. The samples were then divided into tubes, boiled for five minutes, put into the ice bath for five minutes, and centrifuged at 8,000 rpm and 4° C. for 10 minutes. Each of the upper phases was transferred to a new tube by 800 µl, treated with enzymes (DNase/RNase), and put into the ice bath for 10 minutes. Next, 200 µl of 10% TCA/acetone preparation-50% TCA/acetone was added to each tube. The tubes were placed into the ice bath for a period of 1 hour. The samples were then centrifuged at 12,000 rpm and 4° C. for 10 minutes, and the resulting pallets were washed with acetone. The remaining dry powders were kept at −20° C.

Example 2

Separation of Proteins by 2D E-Proteomics

<2-1> Primary Separation of Proteins by Isoelectric Point

Proteins are primarily separated based on isoelectric point. Dry immobilized pH gradient (IPG) strips of 13 cm were added with 250 µl isoelectric point marker containing 50 µg protein and rehydrated over 10 hours. The rehydrated IPG strips were subjected to isoelectric point separation in an IPG phore (GE Healthcare, USA). The isoelectric point separation was carried out for 1 hour at 500 V, for 1 hour at 1,000 V, and finally at 8,000 V until the final accumulated voltage becomes 60,000 V. At this time, the highest current was set to 50 µA per strip. The strips separated by isoelectric point were slowly stirred over a period of 15 minutes in presence of a primary phase equilibrium solution (50 mM Tris-HCl containing 6M urea, 30% glycerol, 2% SDS, bromophenol blue and 1% DTT, pH 8.8). These primary phase equilibrated strips were soaked in a secondary phase equilibrium solution (50 mM Tris-HCl containing 6M urea, 30% glycerol, 2% SDS, bromophenol blue and 2.5% iodoacetamide, pH 8.8) and stirred again over a period of 15 minutes.

<2-2> Secondary Protein Electrophoresis

Proteins are separated in a polyacrylamide gel depending on their molecular weight. A 12.5% sodium dodecyl sulfate polyacrylamide gel was prepared in size of 13 cm through SE 600 Ruby electrophoresis set (Amersham, USA). Phase equilibrated strips were put on the gel, and the gap between the strip and the gel was filled with a sealing Aga. A running buffer (25 mM Tris, 192 mM glycine, 2.5 mM SDS, pH 8.3) was poured into the set, and proteins of the strips were transferred to the gel within the first 20 minutes at 80V, and electrophoresis was carried out for the next 5 hours at 240V. The electrophoresed gel was stained with silver nitrate. In result, by comparing a gel picture of placental proteins in normal pregnancy by 2D electrophoresis (see FIG. 1A) with a gel picture of placental proteins in pregnancy with preeclampsia by 2D electrophoresis (see FIG. 1B), the inventors could verify changes in placental proteins in pregnancy with preeclampsia.

Example 3

Gel Scanning and Gel Image Analysis

The stained gel was scanned through a flatbed scanner (UMAX PowerLook 1100, USA). During scanning, the option of a transmissive type with 300 dpi resolution was chosen. The scanned gel images were analyzed through an image analysis program (Image Master 2D Platinum, GE Healthcare, USA). Based on the image analysis result, proteins showing differences up to 140% or more in two groups of placental samples were selected and finally identified. In result, the inventors checked proteins showing big differences between normal placenta and preeclamptic placenta by electrophoresis shown in FIG. 1 (In FIG. 2, left-hand side: normal cell; right-hand side: gastric cancer cell), and identified 21 proteins with differences in expression between normal placenta and preeclamptic placenta.

Example 4

Protein Identification

The 21 proteins with differences in expression between normal placenta and preeclamptic placenta used were collected and sent to IN2GEN Co., Ltd. for protein mass analysis based on MALDI-TOF MS technique. Peaks of protein mass spectrometry analyzed were searched by MASCOT PMF based on the NCBI database and listed with GeneBank IDs in Table 1 below.

TABLE 1

| Spot NOs | NCBI accession NOs | SEQ ID NOs | protein identification |
|---|---|---|---|
| 1 | 49522865 | SEQ ID NO: 1 | chaperonin |
| 2 | 1208427 | SEQ ID NO: 2 | ER-60 protease |
| 3 | 1167843 | SEQ ID NO: 3 | alpha-enolase |
| 4 | 28178825 | SEQ ID NO: 4 | Isocitrate dehydrogenase 1 |
| 5 | 1633300 | SEQ ID NO: 5 | Aldehyde reductase |
| 6 | 493797 | SEQ ID NO: 6 | chain B, Fidarestat Bonded to human Aldose reductase |
| 7 | 14250132 | SEQ ID NO: 7 | Voltage-dependent anion channel 1 |
| 8 | 4588526 | SEQ ID NO: 8 | Nuclear chloride channel |
| 9 | 5822091 | SEQ ID NO: 9 | Chain H, Cathepsin D |
| 10 | 56081766 | SEQ ID NO: 10 | Phosphoglycerate mutase 1 |
| 11 | 5803013 | SEQ ID NO: 11 | Endoplasmic reticulum protein |
| 12 | 50881968 | SEQ ID NO: 12 | PSMA2 protein |
| 13 | 2204207 | SEQ ID NO: 13 | Glutathione S-transferase |
| 14 | 8249777 | SEQ ID NO: 14 | Ig heavy chain v region |
| 15 | 16924329 | SEQ ID NO: 15 | Smooth muscle myosin alkali light chain |
| 16 | 4557581 | SEQ ID NO: 16 | Fatty acid binding protein |

The above Table 1 presents the analysis result on the 21 proteins obtained by MALDI-TOF MS technique, verifying that all of the 21 proteins except one were expressed remarkably high in the preeclamptic placenta compared with the normal placenta.

Example 5

Protein Analysis and Suggestion of Pathophysiology

The inventors analyzed 17 out of the 21 proteins and confirmed that most of the proteins were associated with placenta metabolism. To be more specific, the inventors analyzed not only functions of those 21 proteins, but also changes in protein expression detected in the preeclamptic placenta compared with that of the normal placenta, wherein the analysis result is listed in Table 2 below.

TABLE 2

| Category | Protein | Relative change (%) |
|---|---|---|
| Structural | Smooth muscle myosin alkali light chain | 191 |
| Antioxidant and detoxicant | Glutathione S-transferase | 177 |
| | Isocitrate dehydrogenase | 155 |
| Stress-related protein remodeling | Chaperonin (heat shock protein 60) | 223 |
| Apoptosis | Voltage-dependent anion channel | 185 |
| | Nuclear-chloride channel | 208 |
| | Chain H, Cathepsin D at pH 7.5 | 245 |
| Reduced NADP+- regeneration | Aldehyde reductase | 142 |
| | Chain B, Fidarestat bound to human aldose | 151 |
| Glycolysis | Phpsphoglycerate mutase | 267 |
| | Alpha enolase | 149 |
| Immuno-remodeling | ER-60 protease | 179 |
| Other | Endoplasmic reticulum protein 29 | 242 |
| | PSMA2 protein | 156 |
| | Ig heavy chain v region | 216 |
| | Fatty acid binding protein 5 | 220 |

Figure 3:
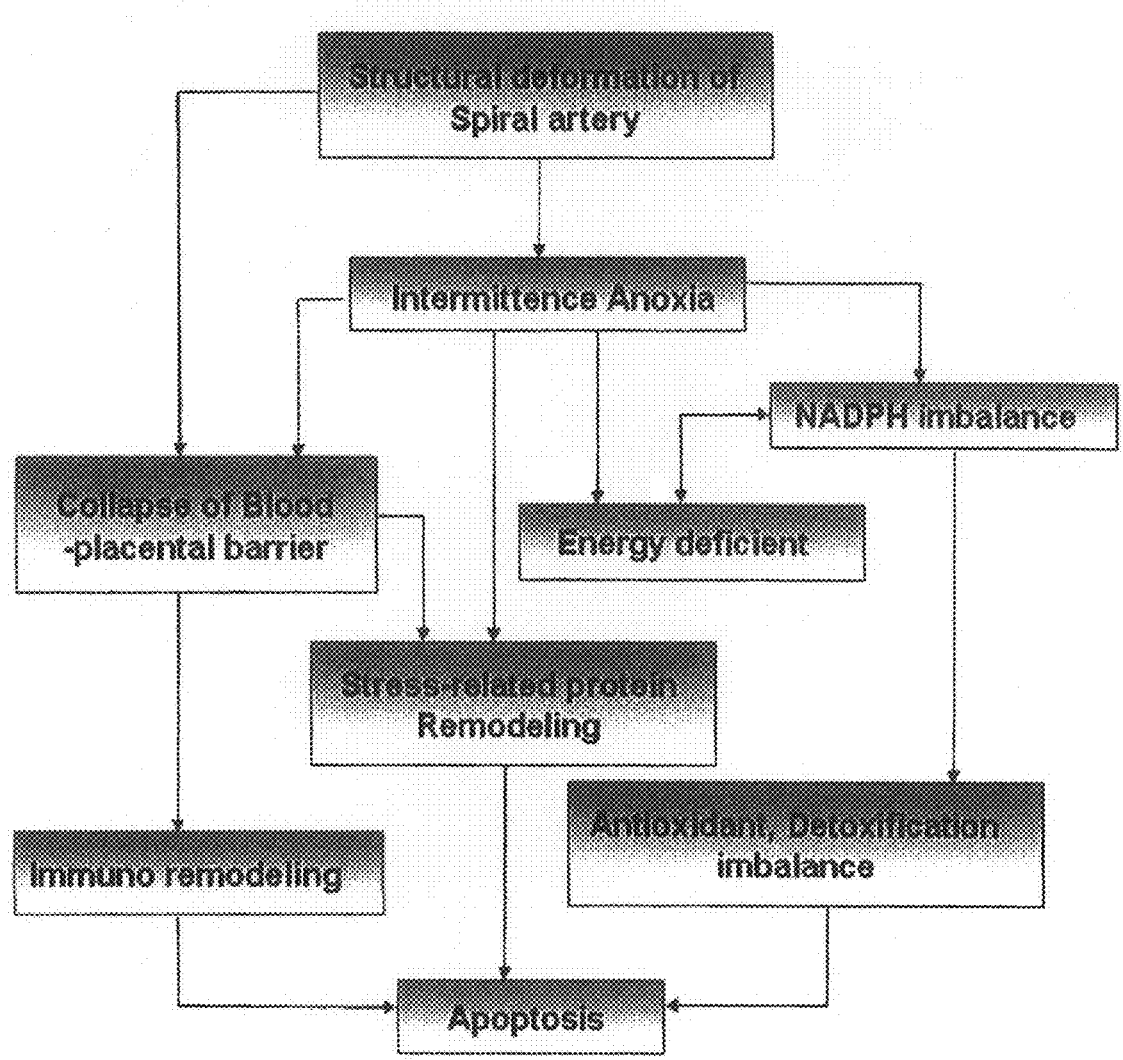
FIG. 3 offers a conceptual diagram suggesting the pathogenesis of preeclampsia on the basis of the analysis of proteins exhibiting different expression in preeclamptic placenta.

The proteins were categorized into different types based on their association with antioxidant activities, recombination related to stress, apoptosis, glycolysis, immunomodulation, or remodeling of reduced NADP such that the pathophysiology of protein-underlying preeclampsia can be presented as shown in FIG. 3.

As discussed above, according to the present invention, the variation in certain protein expression in a preeclamptic placenta can be identified by a 2-D E-proteomics analysis, thus making it possible to present a theory on the pathogenesis of preeclampsia. Further, the screening method and marker of the present invention can screen placental proteins of different expressions in the placenta of a pregnant woman with preeclampsia, and those proteins can be used as a marker for prevention and early treatment of preeclampsia.

While the invention has been shown and described with respect to the preferred embodiments, it will be understood by those skilled in the art that various changes and modifications may be made without departing from the spirit and the scope of the invention as defined in the following claims.

What is claimed is:

1. A method of screening placental proteins responsible for pathophysiology of preeclampsia by 2D E-proteomics analysis, comprising:
   isolating placental proteins from a placental tissue;
   separating the isolated proteins two-dimensionally through 2D electrophoresis; and
   comparing and analyzing the separated proteins based on scanned gel images and differences in the images between normal placental proteins and preeclamptic placental proteins,
   wherein comparing and analyzing the separated proteins comprises selecting proteins having an increased expression of 140% or more in the preeclamptic placental proteins than in the normal placental proteins based on scanned gel images and differences in the images between the normal placental proteins and the preeclamptic placental proteins.

2. The method of claim 1, wherein the proteins are selected from the protein group consisting of chaperonin, ER-60 protease, isocitrate dehydrogenase 1, aldehyde reductase 1, fidaresta chain B bonded to human aldose reductase, voltage-dependent anion channel 1, nuclear chloride channel, cathepsin D chain H, phosphoglycerate mutase 1, endoplasmic reticulum protein, PSMA2 protein, glutathione S-transferase, Ig heavy chain v region, smooth muscle myosin alkali light chain, and fatty acid binding protein.

* * * * *